United States Patent
Takahashi et al.

[11] Patent Number: 5,705,819
[45] Date of Patent: Jan. 6, 1998

[54] EMISSION CT APPARATUS

[75] Inventors: Munehiro Takahashi, Kyoto; Tsunekazu Matsuyama, Kameoka, both of Japan

[73] Assignee: Shimadzu Corporation, Kyoto, Japan

[21] Appl. No.: 382,093

[22] Filed: Jan. 30, 1995

[30] Foreign Application Priority Data

Jan. 31, 1994 [JP] Japan ................... 6-029026

[51] Int. Cl.⁶ .................. G01T 1/161; G01T 1/166
[52] U.S. Cl. ............. 250/363.04; 250/363.02; 250/363.07
[58] Field of Search ............ 250/363.02, 363.04, 250/363.07, 369

[56] References Cited

U.S. PATENT DOCUMENTS

| | | |
|---|---|---|
| 4,582,995 | 4/1986 | Lim et al. . |
| 5,056,020 | 10/1991 | Feldman et al. . |
| 5,075,554 | 12/1991 | Yunker et al. ............ 250/363.05 X |
| 5,103,823 | 4/1992 | Acharya et al. ............ 250/363.04 X |
| 5,164,971 | 11/1992 | Peyret et al. . |
| 5,251,128 | 10/1993 | Crawford . |
| 5,337,231 | 8/1994 | Nowak et al. ............ 250/363.07 X |

FOREIGN PATENT DOCUMENTS

| | | |
|---|---|---|
| 41 36 030 A1 | 5/1992 | Germany . |
| 57-53674 | 3/1982 | Japan ............ 250/363.04 |
| 58-92975 | 6/1983 | Japan ............ 250/363.04 |
| 63-37284 | 2/1988 | Japan ............ 250/363.02 |
| 63-37285 | 2/1988 | Japan ............ 250/363.02 |
| 63-177092 | 7/1988 | Japan ............ 250/363.04 |
| 2 194 870 | 3/1988 | United Kingdom . |

*Primary Examiner*—Edward J. Glick
*Attorney, Agent, or Firm*—Nikaido, Marmelstein, Murray & Oram LLP

[57] ABSTRACT

An emission CT apparatus for detecting, in positions around an examinee, radiation from radioactive nuclides introduced into the examinee and having accumulated in a site of concern, in order to acquire density distribution images (sectional images) of the nuclides in sections of the site of concern. The apparatus comprises a gamma camera for detecting the radiation, a rotary device for revolving the gamma camera stepwise round the examinee, an image memory for collecting image data from the gamma camera for respective time frames defined by dividing a period of time for which the gamma camera stands still at each angular position, a computing unit for determining a center of gravity of the image data in each time frame, an adder for adding image data, with the center of gravity brought into agreement, in each time frame, thereby to obtain image data in a direction of each angular position (view), and an image reconstruct unit for reconstructing an image based on the image data of each view corrected.

16 Claims, 3 Drawing Sheets

EMISSION CT APPARATUS

BACKGROUND OF THE INVENTION

(1) Field of the Invention

This invention relates to an emission CT apparatus of the type having a two-dimensional radiation detector (e.g. a gamma camera) revolvable round an examinee.

(2) Description of the Related Art

The emission CT apparatus having a gamma camera revolvable round an examinee detects, by means of the gamma camera in varied angular positions (views), radiation from single-photon emitting nuclides given to an examinee and having accumulated in an internal organ or the like, and acquires a two-dimensional image from each view. Only one-dimensional distribution data arranged in a predetermined plane (which is perpendicular to an axis of revolution of the gamma camera) may be picked out of the image data acquired as a two-dimensional image from each view. This one-dimensional distribution data may be processed as projection data by a back projection algorithm to reconstruct a density distribution image (slice image) of the nuclides on that plane.

The data may be collected from the respective views in a stepped revolution mode or a continuous revolution mode. In the stepped revolution mode, the gamma camera is revolved stepwise by 6 degrees, for example, and data is collected during each stopping period (e.g. 20 to 60 seconds). In this way, data of 60 views are obtained in all directions through 360 degrees in several tens of minutes. In the continuous revolution mode, the gamma camera is continuously revolved to make a complete circle in one minute. Data is collected every second to obtain data of 60 views in one revolution. This revolution may be effected in a fixed direction or alternately in opposite directions several tens of times, adding together the data obtained from the same view in different revolutions. In either case, images having the same signal-to-noise ratio and the same resolution are realized if the number of views is the same and the data collecting time for each view amounts to the same total.

The above emission CT apparatus of the gamma camera revolution type has a disadvantage of consuming a relatively long time of several tens of minutes in collecting data. Any movement of the examinee during this period would result in generation of artifacts. In most cases, the examinee is a human whose respiratory or other action inevitably moves his or her internal organs and the like. Such a movement, when data collection is carried out over a long period, produces artifacts to impair image quality.

SUMMARY OF THE INVENTION

Having regard to the state of the art noted above, the object of this invention is to provide an improved emission CT apparatus which effectively suppresses generation of artifacts due to an examinee's movement, thereby to realize sectional images of excellent quality.

The above object is fulfilled, according to this invention, by an emission CT apparatus for detecting, in positions around an examinee, radiation from radio-active nuclides introduced into the examinee and having accumulated in a site of concern, in order to acquire density distribution images (sectional images) of the nuclides in sections of the site of concern, the apparatus comprising:

two-dimensional radiation detector for detecting the radiation;

a rotary device for revolving the two-dimensional radiation detector stepwise by a predetermined angle round the examinee;

a data storage for collecting image data from the two-dimensional radiation detector for respective time frames defined by dividing a period of time for which the two-dimensional radiation detector stands still at the predetermined angle;

a computing unit for determining a center of gravity of the image data in each of the time frames;

an adder for adding image data, with the center of gravity brought into agreement, in each of the time frames, thereby to obtain image data in a direction of the predetermined angle (view); and an image reconstruct unit for reconstructing an image by using, as projection data, the image data of each view added, and back projecting the projection data.

The first emission CT apparatus according to this invention having the above construction is an emission CT apparatus of what is known as the stepped revolution/ collection type. To collect data from each view, the period of time for which the two-dimensional radiation detector stops at each angle is divided into a plurality of time frames. The data storage collects image data for each time frame from the two-dimensional radiation detector. Then, the center of gravity (count center) of the image data collected in the data storage is determined for each time frame. While moving images to bring the centers of gravity into agreement, the image data of the multiple time frames belonging to one view are added to obtain image data for that view. Thus, even if the examinee moves during the data collecting period for that view, image data are collected with a correction made with respect to the examinee's movement. An image is reconstructed from the image data with the movement correction for each view. Consequently, sectional images of excellent quality are secured with artifacts due to the movement suppressed.

In the first emission CT apparatus described above, the computing unit, preferably, is operable to determine the center of gravity of simply added image data obtained by simply adding the image data in all of the time frames of each view, and to determine the center of gravity for each of the time frames of each view, and the adder is operable to determine a difference between the center of gravity of the image data in each of the time frames and the center of gravity of the simply added image data of each view, to correct a displacement by moving the image data in each of the time frames by the difference, and to add the image data in each of the time frames corrected.

Preferably, the computing unit and adder are operable, when data collection is effected for a certain view, to correct a displacement of the image data in each of the time frames and add the image data corrected for a preceding view.

A second emission CT apparatus, according to this invention, comprises:

two-dimensional radiation detector for detecting the radiation;

a rotary device for revolving the two-dimensional radiation detector continuously round the examinee;

a data storage for collecting image data for each of predetermined angular ranges from the two-dimensional radiation detector in continuous revolution;

a computing unit for determining a center of gravity of the image data in each of the angular ranges;

an adder for adding image data, with the center of gravity brought into agreement, in corresponding ones of the angular ranges derived from respective continuous revolutions, thereby to obtain image data in each of the angular ranges (view); and an image reconstruct unit for reconstructing an image by using, as projection data, the image data of each view added, and back projecting the projection data.

The second emission CT apparatus noted above is an emission CT apparatus of what is known as the continuous revolution/collection type. The two-dimensional radiation detector in continuous revolution obtains image data. The image data are then stored in the data storage in relation to each predetermined angular range of the revolution. These image data are regarded as image data of a view corresponding to that angular range. Image data of all views are successively obtained from each continuous revolution. The image data of the same view are added together. At this time, the center of gravity of the image data of each view is determined for each revolution, and the image data are added with the centers of gravity brought into agreement. When a required number of revolutions are completed, image data of all the views are obtained in form of accumulation of results from the multiple revolutions. If the examinee moves during the multiple revolutions, a displacement due to the movement will occur between the image data of one view obtained from one revolution and the image data of the same view obtained from the next revolution. These image data are added together with the displacement corrected by bringing the centers of gravity into agreement, thereby to suppress influences of the movement. Consequently, image data of the respective views with the movement correction are secured for use in reconstructing images. The sectional images thereby obtained have excellent quality with artifacts due to the movement suppressed.

In the second emission CT apparatus described above, the rotary device may revolve the two-dimensional radiation detector continuously and alternately in opposite directions, or may revolve the two-dimensional radiation detector continuously in a fixed direction.

Further, in the second emission CT apparatus, the adder, preferably, is operable to determine a difference between the center of gravity of the image data of each view collected from a first revolution of the two-dimensional radiation detector and the center of gravity of the image data of each view collected from a second and subsequent revolutions, to move and correct the image data in each view collected from the second and subsequent revolutions by the difference, and to add the image data in each view corrected to the image data of a corresponding view collected from the first revolution.

Preferably, the adder is operable, when data collection is effected in an (n)th revolution ("n" being an integer 2 or more), to determine the center of gravity and correct a displacement of the image data of each view collected from an (n−1)th revolution and add the image data corrected to image data of a corresponding view collected from the first revolution.

In the first and second emission CT apparatus noted above, the two-dimensional radiation detector may comprise one gamma camera, or a plurality of gamma cameras arranged at equidistant angles.

In the first and second emission CT apparatus, the rotary device, preferably, moves the two-dimensional radiation detector on an elliptic track, with a detection plane of the two-dimensional radiation detector following an ellipse substantially circumscribing a sectional contour of the examinee.

BRIEF DESCRIPTION OF THE DRAWINGS

For the purpose of illustrating the invention, there are shown in the drawings several forms which are presently preferred, it being understood, however, that the invention is not limited to the precise arrangements and instrumentalities shown.

DETAILED DESCRIPTION OF THE PREFERRED EMBODIMENTS

Preferred embodiments of this invention will be described in detail hereinafter with reference to the drawings.

First Embodiment

Figure 1:
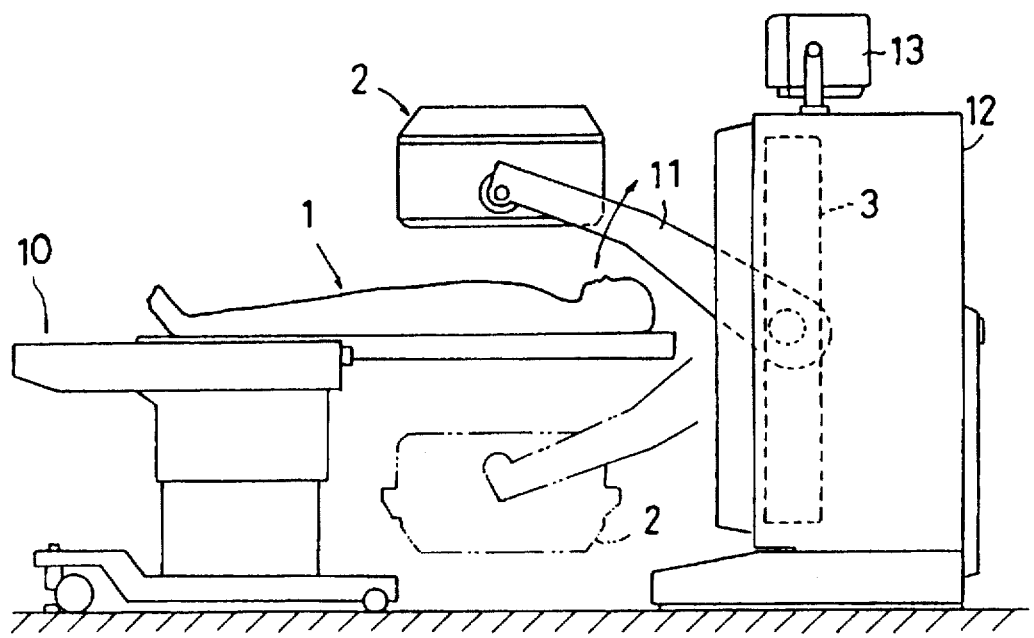
FIG. 1 is a side view of an emission CT apparatus in a first embodiment of this invention.
Figure 2:
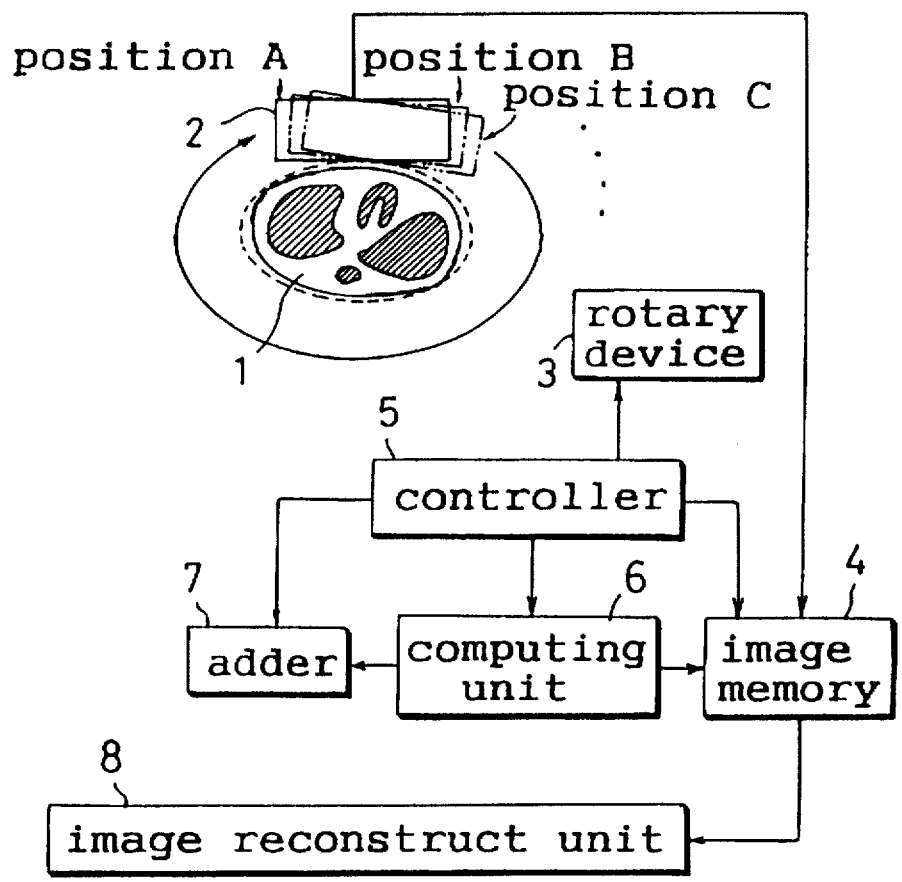
FIG. 2 is a block diagram of the first embodiment.

FIG. 1 is a side view of an emission CT apparatus according to this invention, which collects data in the stepped revolution mode. FIG. 2 is a block diagram of this apparatus.

In FIGS. 1 and 2, an examinee (a human in most cases) 1 is placed on a bed 10. A gamma camera 2 is attached to support arms 11. The support arms 11 are pivotally connected to a rotary device 3 mounted in a frame 12. The rotary device 3 revolves the gamma camera 2 round the examinee 1, and moves the gamma camera 1 toward and away from the examinee 1. The gamma camera 2 is revolvable on an elliptic track as indicated by an arrow in FIG. 2, with a detection plane of the gamma camera 2 following an ellipse (shown in a dotted line) circumscribing a sectional contour of the examinee's body. In such movement, the gamma camera 2 is maintained as close to an outer periphery of the examinee 1 as possible in order to detect radiation with high sensitivity. The rotary device 3 revolves the gamma camera 2 stepwise to move on the elliptic track successively from position A to positions B, C and so on. The frame 12 has a monitor 13 mounted on an upper surface thereof for displaying RI distribution images.

In this embodiment, the gamma camera 2 stops at each of positions A, B, C and so on for 40 seconds during the stepped revolution. Image data derived from the gamma camera 2 during the stopping time is stored in an image memory 4, thereby collecting image data from a view corresponding to each stopping position. The data collecting period for each view is divided into time frames each having a time span of several hundreds of milliseconds to several seconds. This embodiment provides 20 time frames each lasting two seconds. The image memory 4, under control of a controller 5, stores image data in different divisions corresponding to these time frames. After completing the image data collection for the plurality of time frames for the first position A, image data are similarly stored in the different divisions corresponding to the time frames for the next position B.

During the data collecting period for position B, image data in the respective time frames for the previous view (position A) are simply added first. This addition is carried out by an adder 7 under control of the controller 5. Added image data is stored back in a different division in the image memory 4. Being a result of simple addition, the added image data is affected by any movement of the examinee 1 during the 40-second data collecting period. That is, a movement of the examinee's causes a blur.

Further, the center of gravity (count center) of the above simply added image data and the center of gravity (count center) of image data in each time frame for position A are determined during the data collecting period for position B.

The count center is the center of gravity of a count distribution, in respective positions on the two-dimensional detection plane of the gamma camera 2, of radiation (gamma rays) incident on the detection plane. The count center (X, Y) of the image data is derived from the following equation:

$$\text{count center } (X, Y) = \left[ \frac{\sum_y \sum_x (x \cdot C(x,y))}{\sum_y \sum_x C(x,y)}, \frac{\sum_x \sum_y (y \cdot C(x,y))}{\sum_x \sum_y C(x,y)} \right]$$

where C(x,y) represents a count of gamma rays in a given position (x,y) on the two-dimensional detection plane of the gamma camera 2.

Figure 3:
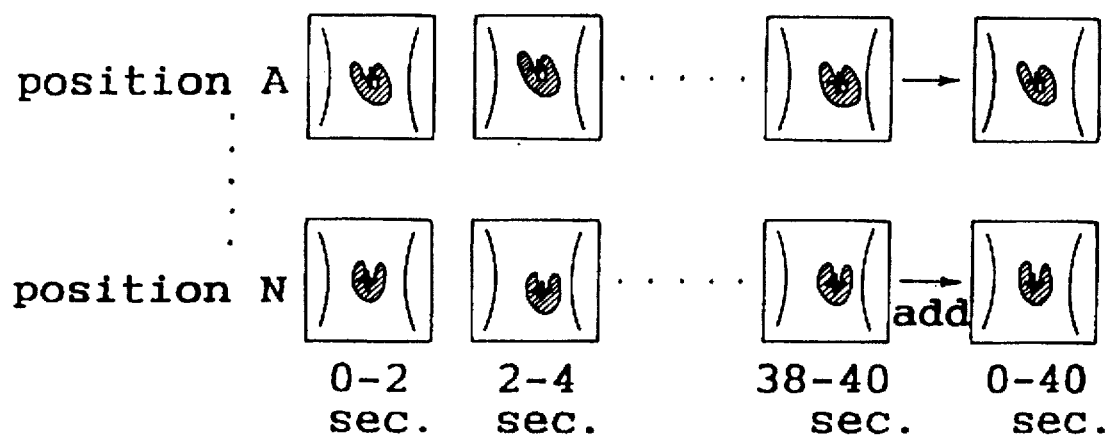
FIG. 3 is an explanatory view of data collection in the first embodiment.

This operation is carried out by a computing unit 6 under control of the controller 5. Specifically, as shown in FIG. 3, image data are obtained for the respective time frames from positions A through N. However, the internal organ under examination is moved by respiratory or other action during the 40-second data collecting period for each position. Under the circumstances, the center of gravity of the image of the organ under examination (indicated in plus sign) is determined for each time frame. Then, a difference between the center of gravity of image data in each time frame and the center of gravity of the simply added image data is determined. The image data in each time frame is added while moving the image data in each time frame by an amount corresponding to the difference. In this way, the image data covering the entire data collecting period of 40 seconds for position A is stored in a different location in the image memory 4 as having been corrected with respect to the influence of the examinee's movement, i.e. with the blur due to the movement corrected to produce a clear image. After the image data with and without the movement correction for the view in position A are stored in the image memory 4, the divisions used for storing the image data of the respective time frames for the view in position A are cleared to be available for storing image data for respective time frames for the view in the next position B.

In this way, the gamma camera 2 revolves stepwise to collect image data from the respective views successively. When the data of one view is collected, the image data with and without the movement correction for the preceding view are stored in the image memory 4. The image data from the respective views with the movement correction are transmitted to an image reconstruct unit 8 where the data are processed by a back projection algorithm to reconstruct sectional images. These sectional images are reconstructed from the image data with the movement correction and free of blurs. Thus, the sectional images have excellent quality with artifacts due to the movement suppressed, and a deterioration in resolution of the images due to the movement remedied.

Second Embodiment

Figure 4:
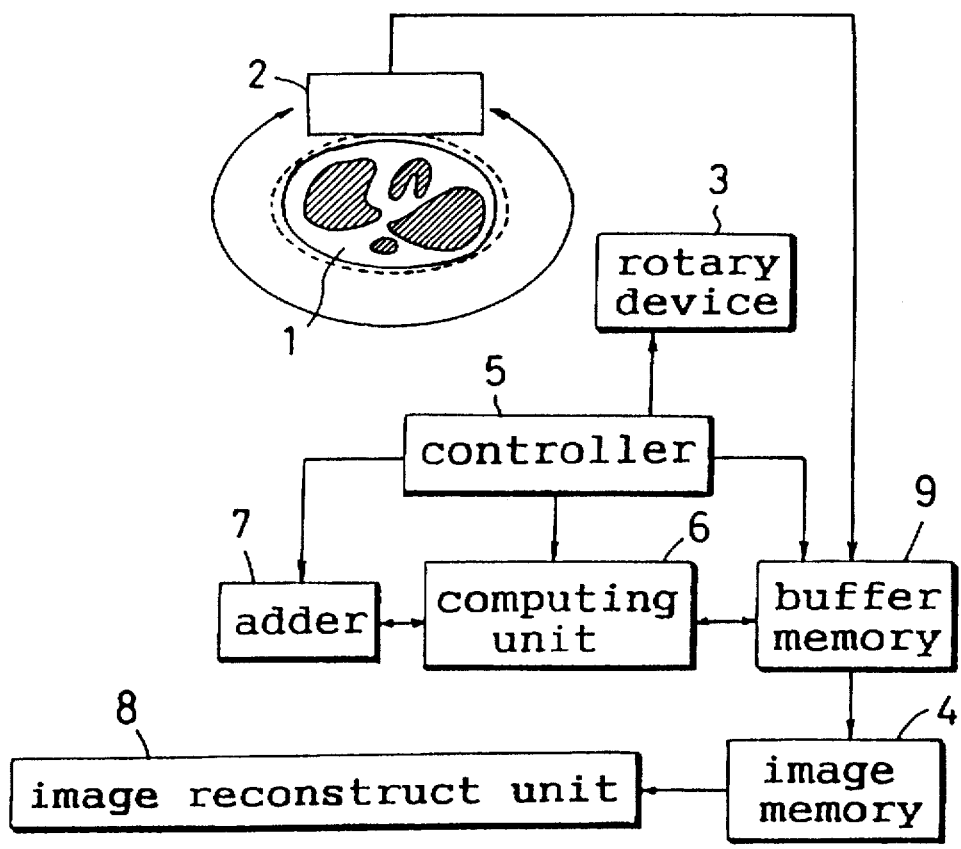
FIG. 4 is a block diagram of a second embodiment of this invention.

FIG. 4 is a block diagram of a second embodiment of this invention. In the second embodiment, this invention is applied to an emission CT apparatus having a gamma camera revolvable continuously to collect data. In FIG. 4, gamma camera 2 is revolvable round an examinee 1 by a rotary device 3 along the same elliptic track as in the embodiment shown in FIG. 2. In this embodiment, however, the gamma camera 2 is continuously revolvable in opposite directions, reversed upon each complete revolution (360°) by the rotary device 3.

Figure 5:
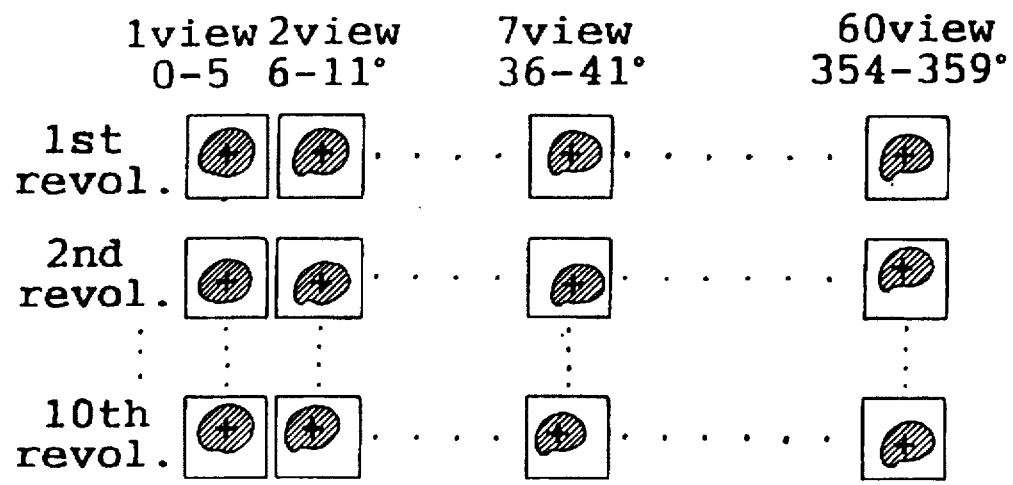
FIG. 5 is an explanatory view of data collection in the second embodiment.

Image data derived from the gamma camera 2 in continuous revolution are stored in a buffer memory 9. The buffer memory 9, under control of a controller 5, stores the data in different areas second by second. The gamma camera 2 makes one complete revolution in one minute, to obtain image data from 60 views in one revolution. Thus, each view has an angular range of six degrees. A first revolution produces image data of views 1 to 60 for the respective angular ranges as shown in FIG. 5.

The first revolution is followed by a second revolution in the opposite direction from 360° to 0°. The buffer memory 9 is divided into four large divisions IB1, IB2, IB3 and IB4. Each large division includes subdivisions for storing image data of views 1 to 60. The image data of views 1 to 60 obtained from the first revolution are stored simultaneously and in parallel in the two large divisions IB1 and IB2. The image data of views obtained second by second from the second revolution are added to the subdivisions of the large division IB2, and in parallel thereto are stored in the large division IB3.

During the second revolution, the center of gravity (count center) of an internal organ under examination is determined for the image data of each view collected from the first revolution. The center of gravity is shown in plus signs in FIG. 5. The operation to determine the center of gravity is carried out by a computing unit 6 under control of the controller 5 as in the first embodiment.

Further, the operation proceeds to a third revolution for successively collecting image data of views 1 to 60 and storing the data in parallel in the large divisions IB2 and IB4. During the third revolution, the center of gravity of the internal organ under examination is determined for the image data of each view collected from the second revolution and stored in the large division IB3. This center of gravity is compared with the center of gravity in the corresponding view image stored in the large division IB1. The image data in the subdivisions of the large division IB3 are shifted so that the corresponding views have an identical center. Then, the image data of the corresponding views are added to the subdivisions of the large division IB1. The shifting and addition of the images are carried out by the computing unit 6 and adder 7 under control of the controller 5. The large division IB3 is cleared after the image data of the respective views collected from the second revolution are transferred from the large division IB3 to the large division IB1. Subsequently, the image data of views obtained from a fourth revolution are stored in parallel in the large divisions IB2 and IB3. During this data collection, the center of gravity is determined for the image data of each view in the large division IB4, and the image data are shifted. The image data processed are added to the large division IB1, and then the large division IB4 is cleared.

When 10 revolutions, for example, are completed, the subdivisions of the large division IB1 of the buffer memory 9 store image data of the respective views derived from the 10 revolutions, with corrections made with respect to a displacement of the internal organ under examination due to a movement of the examinee 1. On the other hand, the subdivisions of the large division IB2 of the buffer memory 9 store simple additions of the image data of the respective views derived from the 10 revolutions. That is, as shown in FIG. 5, the image data of the respective views derived from the respective rotations are added in the vertical direction in FIG. 5, to produce image data of the respective views added upon completion of each revolution. Where 10 revolutions are effected, a total of 10 minutes is consumed. For one view, an interval of one minute on average occurs between two revolutions. During this interval, the internal organ under examination is moved by respiratory action of the examinee 1. Consequently, blurs due to the displacement are produced if the image data of the respective views are simply added in the vertical direction in FIG. 5. Image data of the respective views without such blurs are secured by adding the data after correcting the displacement and shifting the image data of the respective views derived from the second and subsequent revolutions so that the centers of gravity register with the center of the image data derived from the first revolution.

The image data of the respective views with and without the movement correction stored in the buffer memory 9 are transmitted to an image memory 4. Further, the image data with the movement correction are transmitted to an image reconstruct unit 8 where the data are processed by a back projection algorithm to reconstruct sectional images. These sectional images are reconstructed from the image data with the movement correction and free of blurs. Thus, the sectional images have excellent quality with artifacts due to the movement suppressed, and a deterioration in resolution of the images due to the movement remedied.

Figure 6:
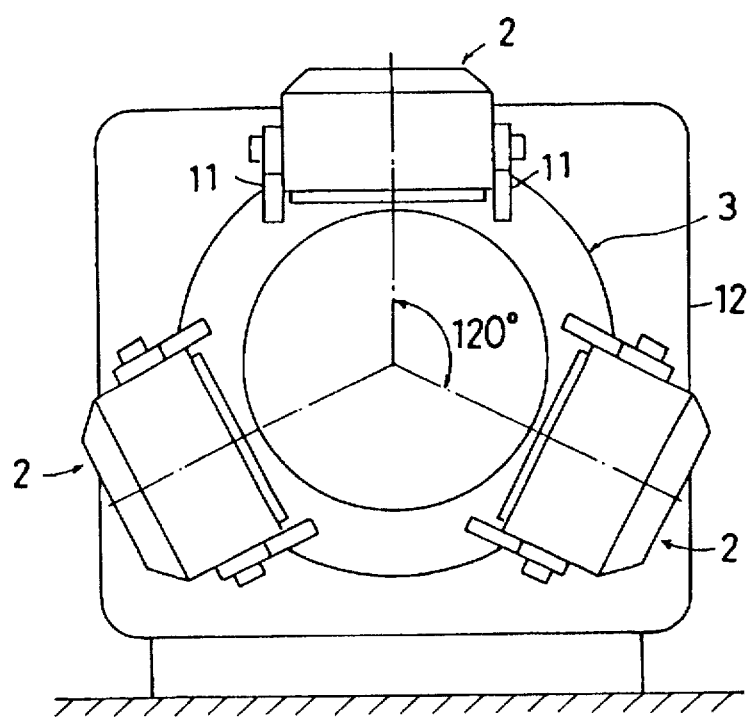
FIG. 6 is a front view of an emission CT apparatus to which this invention is applicable and which has three gamma cameras.

In the two embodiments described above, the image data of the respective views without the movement correction are collected besides the image data with the movement correction. The former are used for comparing and confirming the image data before and after the correction. However, such uncorrected data need not be collected. The constructions of the memories 4 and 9 in the two embodiments are only exemplary; other constructions are possible as long as the memories perform similar functions as data storage. In the second embodiment, the direction of revolution is reversed for each successive revolution to avoid excessive twisting of cables connected to the gamma camera 2. The gamma camera 2 may be revolved continuously in the same direction by employing a slip ring or spiral cables to absorb the twisting. Both of the embodiments described are the single detector type to revolve one gamma camera 2. This invention is, of course, equally applicable to a multiple detector type apparatus having two gamma cameras, or three gamma cameras 2 as shown in FIG. 6, or more than three gamma cameras, arranged at equidistant angles and revolvable in unison.

The present invention may be embodied in other specific forms without departing from the spirit or essential attributes thereof and, accordingly, reference should be made to the appended claims, rather than to the foregoing specification, as indicating the scope of the invention.

What is claimed is:

1. An emission CT apparatus for detecting, in positions around an examinee, radiation from radioactive nuclides introduced into the examinee and having accumulated in a site of concern, in order to acquire density distribution images (sectional images) of the nuclides in sections of the site of concern, said apparatus comprising:

two-dimensional radiation detecting means for detecting said radiation;

rotary means for revolving said two-dimensional radiation detecting means stepwise by predetermined angle increments around said examinee, said detection means stopping at each increment to collect image data for a view;

data storage means for collecting the image data from said two-dimensional radiation detecting means for a plurality of respective time frames defined by dividing a time during which said detection means is stopped at each increment into the respective time frames;

computing means for determining a center of gravity of the image data in each of said respective time frames, and for determining a center of gravity of simply added image data obtained by simply adding the image data in the plurality of respective time frames belonging to each view;

adding means for adding said image data in said respective time frames belonging to each view, thereby generating said simply added image data, said adding means also determining a difference between the center of gravity of said image data in each respective time frame belonging to each view and the center of gravity of said simply added image data, correcting a displacement by moving the image data in said each respective time frame by the difference corresponding to the respective time frame, and adding the image data of corrected time frames, thereby generating corrected image data; and image reconstruct means for reconstructing an image by using, as projection data, said corrected image data obtained for each view, and back projecting said projection data.

2. An apparatus as defined in claim 1, wherein said two-dimensional radiation detecting means comprises one gamma camera.

3. An apparatus as defined in claim 1, wherein said two-dimensional radiation detecting means comprises a plurality of gamma cameras arranged at equidistant angles.

4. An apparatus as defined in claim 1, wherein said rotary means is operable to move said two-dimensional radiation detecting means on an elliptic track, with a detection plane of said two-dimensional radiation detecting means following an ellipse substantially circumscribing a sectional contour of said examinee.

5. An apparatus as defined in claim 1, wherein said rotary means advances said detecting means for a subsequent view, and wherein said computing means and said adding means are operated, while data collection is effected for the subsequent view, to correct the displacement of said image data in each of said respective time frames and add said image data corrected for a preceding view.

6. An emission CT apparatus for detecting, in positions around an examinee, radiation from radioactive nuclides introduced into the examinee and having accumulated in a site of concern, in order to acquire density distribution images (sectional images) of the nuclides in sections of the site of concern, said apparatus comprising:

two-dimensional radiation detecting means for detecting said radiation;

rotary means for revolving said two-dimensional radiation detecting means in a first continuous revolution and a second continuous revolution around said examinee;

data storage means for collecting image data from said two-dimensional radiation detecting means, during said first continuous revolution and said second continuous revolution, for each of a plurality of angular positions around a perimeter defined by a revolving path of said two-dimensional radiation detecting means, each position of said plurality of angular positions forming a view, said plurality of positions being the same for each of said first and second continuous revolutions, thereby generating a plurality of image data for each view;

computing means for determining a center of gravity of said image data in each said view;

adding means for obtaining added image data for each view by adding said plurality of image data belonging to each view, with said center of gravity brought into agreement; and image reconstruct means for reconstructing an image by using, as projection data, said added image data obtained for each view, and back projecting said projection data.

7. An apparatus as defined in claim 6, wherein said two-dimensional radiation detecting means comprises one gamma camera.

8. An apparatus as defined in claim 6, wherein said two-dimensional radiation detecting means comprises a plurality of gamma cameras arranged at equidistant angles.

9. An apparatus as defined in claim 6, wherein said rotary means is operable to move said two-dimensional radiation detecting means on an elliptic track, with a detection plane of said two-dimensional radiation detecting means following an ellipse substantially circumscribing a sectional contour of said examinee.

10. An apparatus as defined in claim 6, wherein said first continuous revolution is in a first direction, and wherein said second continuous revolution is in a second direction, opposite from said first direction.

11. An apparatus as recited in claim 10, wherein said rotating means is operable to revolve said two-dimensional radiation detecting means alternately and in repeated first and second continuous revolutions in the first and second directions.

12. An apparatus as defined in claim 6, wherein said rotary means revolves said two-dimensional radiation detecting means continuously in the first direction.

13. An apparatus as defined in claim 6, wherein said adding means is operable to determine a difference between the center of gravity of said image data of each view collected from the first continuous revolution of said two-dimensional radiation detecting means and the center of gravity of said image data of each view collected from the second and subsequent revolutions, to move and correct said image data in each view collected from said second and subsequent revolutions by said difference, and to add said image data in each view corrected to said image data of a corresponding view collected from said first continuous revolution.

14. An apparatus as defined in claim 13, wherein said adding means is operable, when data collection is effected in an (n)th revolution ("n" being an integer 2 or more), to determine the center of gravity and correct a displacement of said image data of each view collected from an (n−1)th revolution and add said image data corrected to said image data of a corresponding view collected from the first continuous revolution.

15. An emission CT apparatus as recited in claim 6, wherein said plurality of angular positions are defined by dividing the perimeter by a desired number of positions wherein each position of said plurality of positions are disposed at equiangular positions around a rotational axis of the two-dimensional radiation detecting means.

16. An emission CT apparatus as recited in claim 6, wherein the plurality of image data for each view comprises one set of image data for each corresponding angular position in a plurality of continuous revolutions of said two-dimensional radiation detecting means.

\* \* \* \* \*